US00PP24567P2

(12) United States Plant Patent
Eskelund

(10) Patent No.: US PP24,567 P2
(45) Date of Patent: Jun. 24, 2014

(54) ROSE PLANT NAMED 'EVERA607'

(50) Latin Name: *Rosa hybrida*
Varietal Denomination: Evera607

(75) Inventor: Rosa Eskelund, Fåborg (DK)

(73) Assignee: Roses Forever ApS, Faborg (DK)

( * ) Notice: Subject to any disclaimer, the term of this patent is extended or adjusted under 35 U.S.C. 154(b) by 176 days.

(21) Appl. No.: 13/506,817

(22) Filed: May 17, 2012

(51) Int. Cl.
*A01H 5/00* (2006.01)

(52) U.S. Cl.
USPC ..... Plt./117

(58) Field of Classification Search
USPC ..... Plt./117, 103, 124, 133, 144
See application file for complete search history.

*Primary Examiner* — June Hwu
(74) *Attorney, Agent, or Firm* — C. A. Whealy

(57) ABSTRACT

A new and distinct cultivar of Rose plant named 'Evera607', characterized by its upright and mounding plant habit; dark green-colored leaflets; large white-colored flowers; flowers held upright on strong and erect peduncles; and good post-production longevity.

3 Drawing Sheets

Botanical designation: *Rosa hybrida.*
Cultivar denomination: 'EVERA607'.

BACKGROUND OF THE INVENTION

The present Invention relates to a new and distinct cultivar of Rose plant, botanically known as *Rosa hybrida,* commercially used as a potted Rose plant and hereinafter referred to by the name 'Evera607'.

The new Rose plant is a product of a planned breeding program conducted by the Inventor in Fåborg, Denmark. The objective of the breeding program was to develop new uniform potted Rose varieties with novel and attractive flower colors, disease resistance and excellent postproduction longevity.

The new Rose plant originated from an open-pollination made by the Inventor in April, 2008 of *Rosa hybrida* 'Evera209', disclosed in U.S. Plant Pat. No. 21,468, as the female, or seed, parent with an unknown proprietary Rose selection as the male, or pollen, parent. The new Rose plant was discovered and selected by the Inventor in September, 2009 as a single flowering plant within the progeny of the stated open-pollination in a controlled greenhouse environment in Fåborg, Denmark.

Asexual reproduction of the new Rose plant by cuttings in a controlled greenhouse environment at Fåborg, Denmark since October, 2009 has shown that the unique features of this new Rose plant are stable and reproduced true to type in successive generations of asexual reproduction.

SUMMARY OF THE INVENTION

The following traits have been repeatedly observed and are determined to be the unique characteristics of 'Evera607'. These characteristics in combination distinguish 'Evera607' as a new and distinct Rose plant:

1. Upright and mounding plant habit.
2. Dark green-colored leaflets.
3. Large white-colored flowers.
4. Flowers held upright on strong and erect peduncles.
5. Good postproduction longevity.

Plants of the new Rose differ from plants of the female parent, 'Evera209' in the following characteristics:

1. Stems of plants of the new Rose are slightly pubescent whereas stems of plants of 'Evera209' are glabrous.
2. Plants of the new Rose have larger flowers than plants of 'Evera209'.
3. Flowers of plants of the new Rose are longer lasting than flowers of plants of 'Evera209'.

Plants of the new Rose can be compared to plants of the Rose 'Evera211', disclosed in U.S. Plant Pat. No. 21,470. In side-by-side comparisons conducted in Fåborg, Denmark, plants of the new Rose differed from plants of 'Evera21' in the following characteristics:

1. Plants of the new Rose had longer flower buds than plants of 'Evera211'.
2. Plants of the new Rose had thicker and stronger peduncles than plants of 'Evera211'.
3. Plants of the new Rose and 'Evera211' differed in flower color as plants of 'Evera211' had yellow-colored flowers.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph on the first sheet comprises a side perspective view of a typical plant of 'Evera607' grown in a container.

The photograph at the top of the second sheet is a close-up view of a typical flower bud of 'Evera607'.

The photograph at the bottom of the second sheet is a close-up view of a typical flower of 'Evera607'.

The photograph at the top of the third sheet is a close-up view of the upper surface of a typical leaf.

The photograph at the bottom of the third sheet is a close-up view of the lower surface of a typical leaf.

DETAILED BOTANICAL DESCRIPTION

Plants of the new Rose have not been observed under all possible environmental conditions and cultural practices. The phenotype may vary somewhat with variations in environmental conditions such as temperature and light intensity, without, however, any variance in genotype. The aforementioned photographs, following observations and measurements describe plants grown during the spring in Sabro, Denmark, in a glass-covered greenhouse and under cultural practices typical of commercial potted Rose production. Plants were grown in 10-cm containers, pinched two times and were three months old when the photographs and description were taken. During the production of the plants, day temperatures averaged 21° C., night temperatures averaged 19° C. and light levels ranged from 8,000 to 10,000 lux. In the following description, color references are made to The Royal Horticultural Society Colour Chart, 2007 Edition, except where general terms of ordinary dictionary significance are used.

Botanical classification: *Rosa hybrida* 'Evera607'.

Parentage:

*Female, or seed, parent.*—*Rosa hybrida* 'Evera209', disclosed in U.S. Plant Pat. No. 21,468.

*Male, or pollen, parent.*—Unknown proprietary selection of *Rosa hybrida,* not patented.

Propagation:

*Type.*—By cuttings.

*Time to initiate roots, summer.*—About twelve days at 24° C.

*Time to initiate roots, winter.*—About twelve days at 21° C.

*Time to produce a rooted young plant, summer.*—About 28 days at 24° C.

*Time to produce a rooted young plant, winter.*—About 32 days at 24° C.

*Root description.*—Fibrous, fine to thick; white in color.

*Rooting habit.*—Freely branching; medium density.

Plant description:

*Plant and growth habit.*—Upright and mounding plant habit; moderately vigorous growth habit; pinching enhances lateral branch development.

*Plant height.*—About 18 cm to 25 cm.

*Plant width* (*spread*).—About 16 cm to 25 cm.

*Lateral branches.*—Length: About 16 cm to 24 cm. Diameter: About 4 mm to 5 mm. Internode length: About 1 cm to 1.5 cm. Strength: Strong. Texture: Slightly pubescent. Color: Close to 137C. Thorns: Density: About two to five per linear centimeter. Shape: Triangular with sharp acuminate apices. Height: About 2 mm to 5 mm. Diameter, at base: About 1 mm to 3 mm. Color, immature: Close to 145B. Color, mature: Close to 165B.

Foliage description:

*Arrangement.*—Alternate; compound with three or five leaflets per leaf.

*Leaf length.*—About 5 cm to 8 cm.

*Leaf width.*—About 5 cm to 6 cm.

*Terminal leaflet length.*—About 3 cm to 4 cm.

*Terminal leaflet width.*—About 2 cm to 2.5 cm.

*Lateral leaflet length.*—About 2.2 cm to 3.5 cm.

*Lateral leaflet width.*—About 1.5 cm to 2.3 cm.

*Leaflet shape.*—Ovate.

*Leaflet apex.*—Acute.

*Leaflet base.*—Obtuse.

*Leaflet margin.*—Serrulate.

*Leaflet texture, upper and lower surfaces.*—Smooth, glabrous; leathery.

*Leaflet venation pattern.*—Pinnate; reticulate.

*Leaflet color.*—Developing leaflets, upper surface: Close to 137A. Developing leaflets, lower surface: Close to 148A. Fully developed, upper surface: Close to N137A; venation, close to 144A. Fully developed, lower surface: Close to 148A; venation, close to 146C.

*Petioles.*—Leaf petiole length: About 1.2 cm to 2 cm. Leaf petiole diameter: About 1 mm. Leaflet petiole length: About 1 mm to 2 mm. Leaflet petiole diameter: About 0.5 mm to 1 mm. Leaf petiole texture, upper and lower surfaces: Sparsely pubescent. Leaflet petiole texture, upper and lower surfaces: Pubescent. Leaf and leaflet petiole color, upper surface: Close to 146A tinged with close to 187A. Leaf and leaflet petiole color, lower surface: Close to 146B.

*Stipules.*—Quantity: Two per leaf. Length: About 3 mm to 6 mm. Width: About 0.5 mm to 1 mm. Shape: Lanceolate. Apex: Acuminate. Base: Truncate; sessile. Margin: Mostly entire; ciliate. Texture, upper and lower surfaces: Smooth, glabrous; leathery. Color, upper surface: Close to 146A. Color, lower surface: Close to 146B.

Flower description:

*Flower type and habit.*—Large double flowers with numerous petals; consistently symmetrical rosette flowers; flowers borne on strong and erect peduncles with one terminal flower per lateral branch.

*Flowering season.*—Year-round under greenhouse conditions, optimal flowering from spring through autumn under garden conditions; flowering intermittent; plants begin flowering about 80 days after planting.

*Flower longevity on plant.*—Good postproduction longevity, flowers last about four weeks; flowers persistent.

*Fragrance.*—Moderately fragrant; pleasant.

*Flower diameter.*—About 6 cm to 7 cm.

*Flower depth* (*height*).—About 3 cm to 3.5 cm.

*Flower buds.*—Shape: Ovoid. Length: About 1.8 cm to 2.4 cm. Diameter: About 1.5 cm to 1.8 cm. Color: Close to 144A.

*Petals.*—Quantity: Numerous; about 105 per flower arranged in numerous whorls. Length: About 1.5 cm to 3.5 cm. Width: About 2 cm to 4 cm. Shape: Obovate to broadly obovate. Apex: Rounded to cuspidate. Base: Attenuate. Margin: Entire. Texture, upper and lower surfaces: Smooth, glabrous; satiny. Color: When opening, upper and lower surfaces: Close to 157C. Fully opened, upper and lower surfaces: Close to 157D; color does not change with development.

*Sepals.*—Quantity and arrangement: Typically five in a single star-shaped whorl. Length: About 2 cm to 2.5 cm. Width: About 8 mm to 12 mm. Shape: Lanceolate. Apex: Pointed, caudate. Base: Truncate. Margin: Entire. Texture, upper and lower surfaces: Pubescent; leathery. Color: When opening and fully opened, upper surface: Close to 143D. When opening and fully opened, lower surface: Close to 143A.

*Peduncles.*—Strength: Strong. Aspect: Erect. Length: About 1.5 cm to 3 cm. Diameter: About 4 mm to 5 mm. Texture: Pubescent. Color: Close to 143B.

*Reproductive organs.*—Stamens: Quantity per flower: About 50. Anther length: About 2 mm to 3 mm. Anther shape: Reniform. Anther color: Close to 13A. Filament color: Close to 150A. Pollen amount: None observed. Pistils: Quantity per flower: About 50. Pistil length: About 3 mm to 5 mm. Stigma color: Close to 150B. Style length: About 2 mm to 3 mm. Style color: Close to 150B. Receptacle shape: Cup-shaped. Receptacle height: About 1 cm. Receptacle diameter: About 1 cm. Receptacle texture: Smooth, glabrous. Receptacle color: Close to 144A. Fruits and seeds: Fruit and seed production have not been observed on plants of the new Rose.

Pathogen & pest resistance: Plants of the new Rose have not been observed to be resistant to pathogens and pests common to Rose plants.

It is claimed:

1. A new and distinct Rose plant named 'Evera607' as illustrated and described.

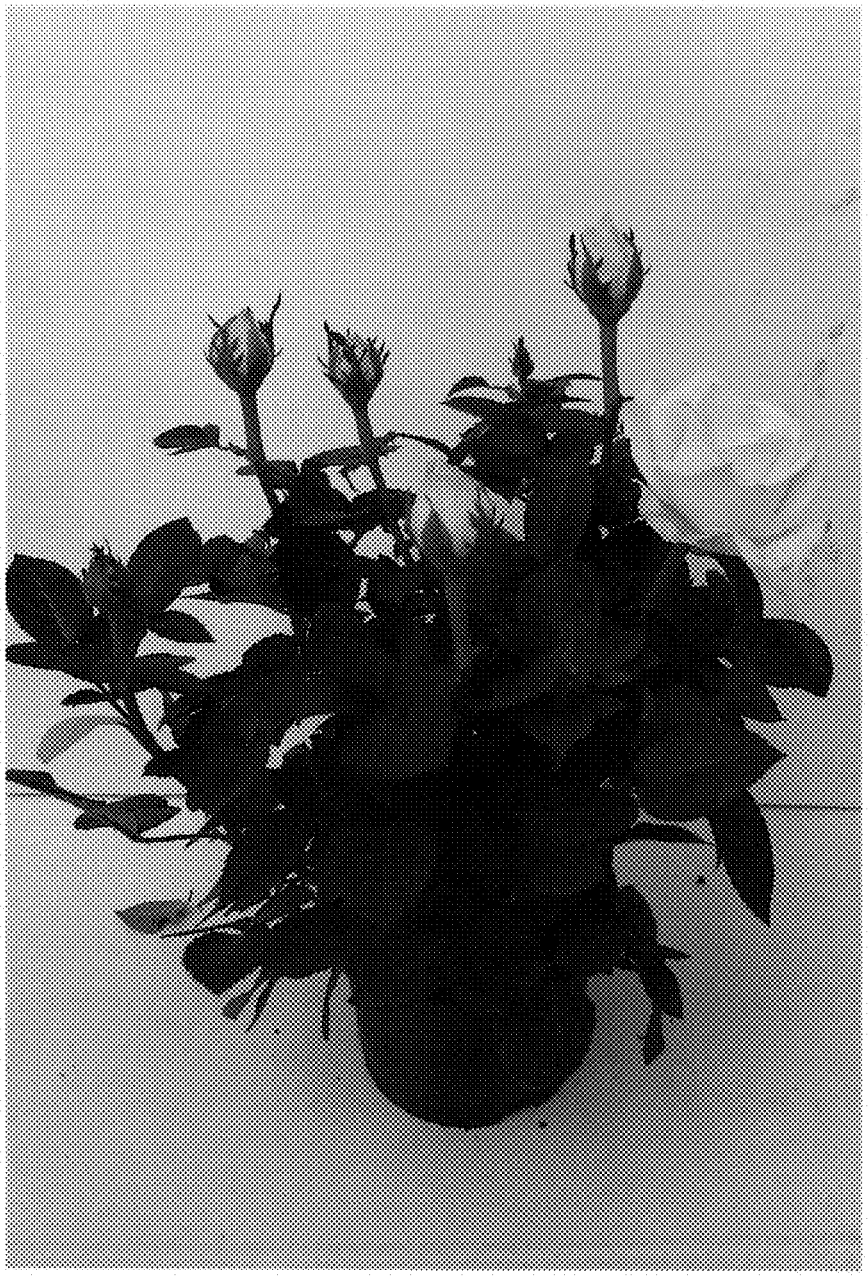

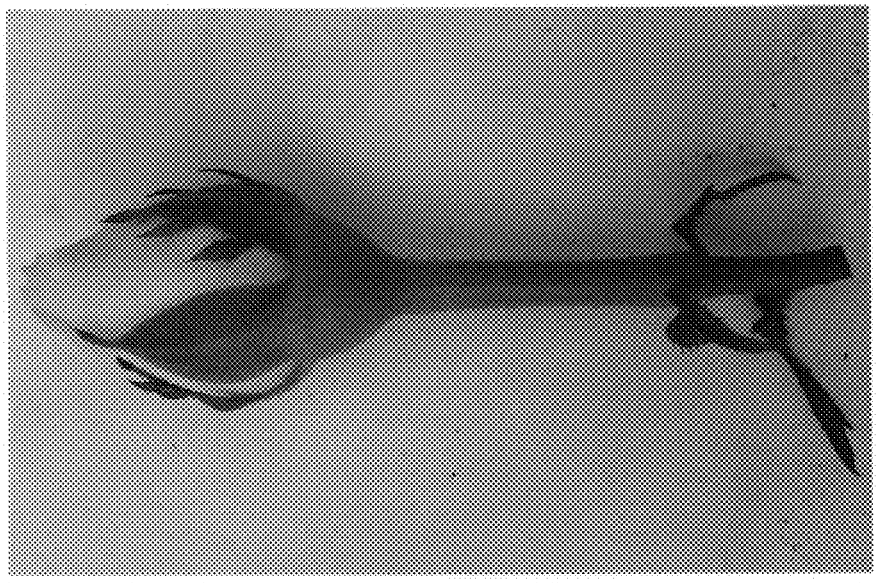
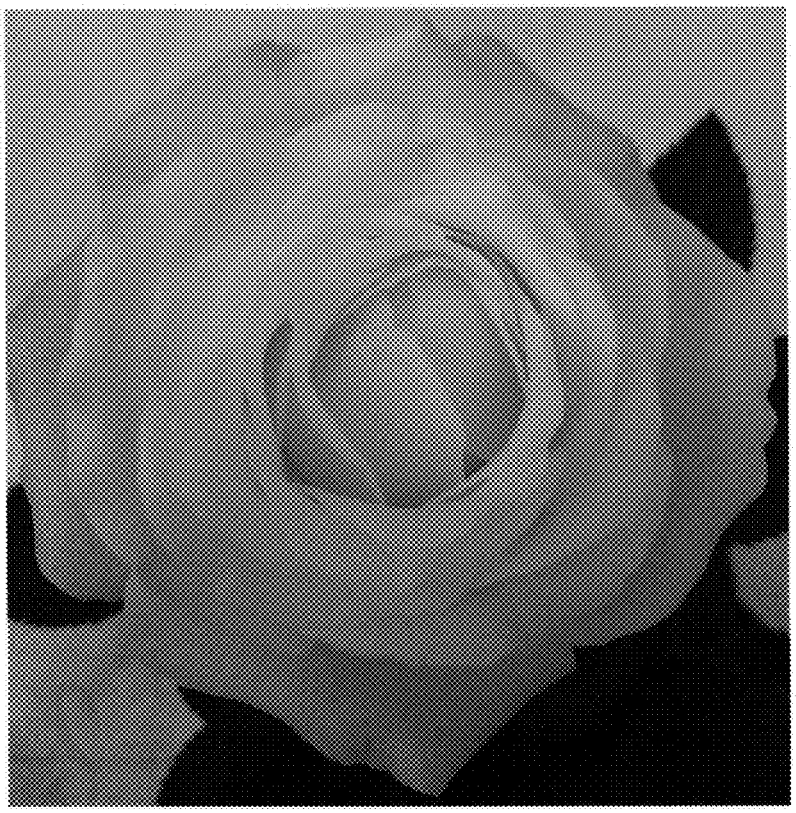

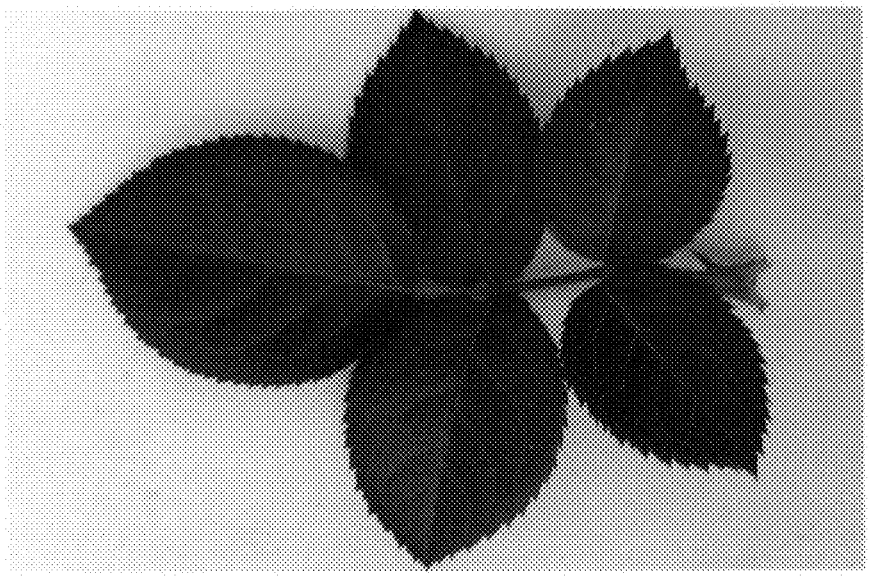
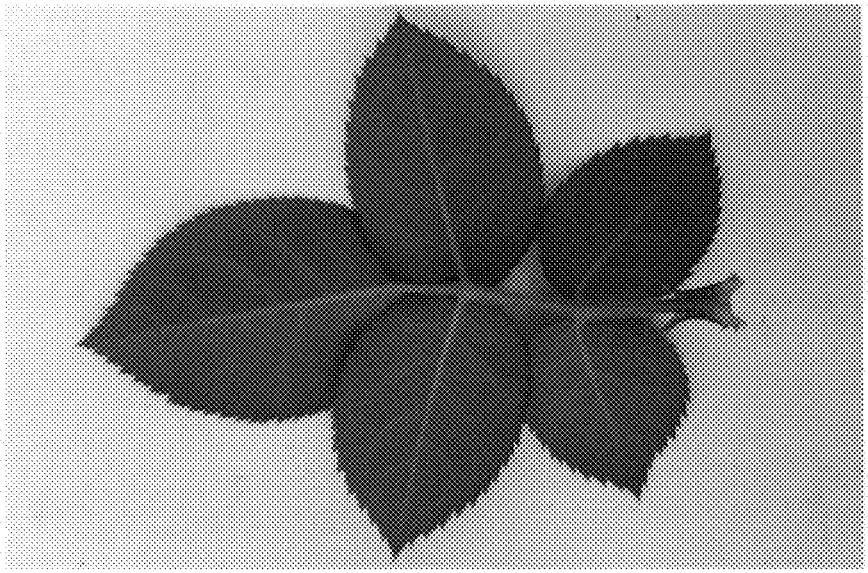

* * * * *